United States Patent [19]

Arimura et al.

[11] Patent Number: 5,128,242
[45] Date of Patent: Jul. 7, 1992

[54] HYPOTHALAMIC POLYPEPTIDES WITH ADENYLATE CYCLASE STIMULATING ACTIVITY

[75] Inventors: Akira Arimura; Atsuro Miyata, both of New Orleans, La.

[73] Assignee: The Administrators of the Tulane Educational Fund, New Orleans, La.

[21] Appl. No.: 367,817

[22] Filed: Jun. 19, 1989

[51] Int. Cl.$^5$ .................. G01N 33/567; A61K 37/02; C07K 7/10
[52] U.S. Cl. .................... 435/7.21; 435/7.1; 435/7.4; 514/12; 530/324; 530/323; 930/170; 930/DIG. 800; 930/DIG. 821; 930/DIG. 820; 930/120
[58] Field of Search .............. 530/324, 323; 435/4, 435/7.21, 7.1, 7.4; 514/12; 930/170, 120, DIG. 820, DIG. 821, DIG. 800

[56] References Cited

U.S. PATENT DOCUMENTS 4,757,133 7/1988 Ito et al. ............................. 530/324
4,840,785 6/1989 Gafuelin et al. ..................... 514/12

FOREIGN PATENT DOCUMENTS 0184309 6/1986 European Pat. Off. .
8806598 9/1988 PCT Int'l Appl. ................. 530/324

OTHER PUBLICATIONS

Robberecht et al., Peptides, 5(5), pp. 877-881, (1984) [Chem. Abs. 102(3): 17817u]
Itoh et al., Nature (London), 304 (5926) pp. 547-549 (1983), [Chem. Abs. vol. 100(11), 805777q].
Yajima et al., Int. J. Pept. Protein Res., vol. 16(1), pp. 33-47 (1980), [Chem. Abs. 94(5); 31063t].
Dimaline et al., Biochem. Biophys. Acta, 930(1), pp. 97-100 (1987), [Chem. Abs. vol. 107(19), 170905u].
Vandermeers et al., Eur. J. Biochem. vol. 164(2), pp. 321-327, (1987) [Chem. Abs. 106(23) 191452pj.
Gourlet et al., Collog. Inserm, 174(Forum Dept., 2nd, 1988), pp. 151-154 (1989), [Chem. Abs. 111(3), 18055s].
Tachibana et al., Pept. Chem., vol. date 1989, pp. 481-486 (1988), [Chem. Abs. 109(15), 122635a].
Wiik, Regul. Dept. 20(4), pp. 323-333 (1988), [Chem. Abs. 108(19) 161860u].
Etgen, J. Neurosie, vol. 3(12), pp. 2487-2493 (1983), [Chem. Abs. vol. 100(9), 62383u].
Harper et al., J. Cyclic Nucleo Res. 1:207-218, 1975.
Kaneko et al., Encodrinol, Japan, S.R. 1:7-10, 1980.
Smith et al., Membranes and Genetic Disease, 113-135, 1982.
Hoosein et al., Febs. Letters, 178:83-86, 1984.
Raizada et al., Am. J. Physiol., 247:C364-372, 1984.
Arimura et al., Peptides, 5:Suppl. 1, 41-44, 1984.
Culler et al., Am. J. Physiol., 247 (Endocrinol. Metab. 10):E609-E615, 1984.
Clarke et al., J. Biol. Chem., vol. 259, No. 19, pp. 11672-11675, 1984.
Vigh and Schally, Peptides, vol. 5, Suppl. 1, pp. 241-247, 1984.
Robberecht et al., Endocrinology, 117:1759-1764, 1985.
Christophe et al., Peptides, 7:101-107, 1986.
Robberecht et al., Peptides, 7:53-59, 1986.
Rosselin, G., Peptides, 7:89-100, 1986.
Brenneman et al., J. Cell Bio., 104:1603-1610, 1987.
Brenneman et al., Nature, 335:639-642, 1988.

Primary Examiner—Lester L. Lee
Assistant Examiner—T. Wessendorf
Attorney, Agent, or Firm—Pennie & Edmonds

[57] ABSTRACT

The present invention relates to peptides having adenylate cyclase stimulating activity. The peptides all have at least the sequence His-Ser-Asp-Gly-Ile-Phe-Thr-Asp-Ser-Tyr-Ser-Arg-Tyr- Arg-Lys-Gln-Met-Ala-Val-Lys-Lys-Tyr-Leu-Ala-Ala-Val-Leu-.

26 Claims, 7 Drawing Sheets

PITUITARY ADENYLATE CYCLASE ACTIVATION IN VITRO

—□— PACAP38
—♦— PACAP27*
—■— Syn pVIP
—●— Syn PACAP38

* AMIDE

```
                   1                                       10                                      20
PACAP38:    His-Ser-Asp-Gly-Ile-Phe-Thr-Asp-Ser-Tyr-Ser-Arg-Tyr-Arg-Lys-Gln-Met-Ala-Val-Lys
ovine HP:   His-Ser-Asp-Gly-Ile-Phe-Thr-Asp-Ser-Tyr-Ser-Arg-Tyr-Arg-Lys-Gln-Met-Ala-Val-Lys----
VIP:        His-Ser-Asp-Ala-Val-Phe-Thr-Asp-Asn-Tyr-Thr-Arg-Leu-Arg-Lys-Gln-Met-Ala-Val-Lys
ovine GHRH: Tyr-Ala-Asp-Ala-Ile-Phe-Thr-Asn-Ser-Tyr-Arg-Lys-Ile-Leu-Gly-Gln-Leu-Ser-Ala-Arg
PHI:        His-Ala-Asp-Gly-Val-Phe-Thr-Ser-Asp-Phe-Ser-Arg-Leu-Leu-Gly-Gln-Leu-Ser-Ala-Lys
Secretin:   His-Ser-Asp-Gly-Thr-Phe-Thr-Ser-Glu-Leu-Ser-Arg-Leu-Arg-Asp-Ser-Ala-Arg-Leu-Gln
Glucagon:   His-Ser-Gln-Gly-Thr-Phe-Thr-Ser-Asp-Tyr-Ser-Lys-Tyr-Leu-Asp-Ser-Arg-Arg-Ala-Gln 21                                      30
            -Lys-Tyr-Leu-Ala-Ala-Val-Leu-Gly-Lys-Arg-Tyr-Lys-Gln-Arg-Val-Lys-Asn-Lys-NH2
            -Lys-Tyr-Leu-Asn-Ser-Ile-Leu-Asn-NH2
            -Lys-Leu-Leu-Gln-Asp-Ile-Met-Asn-Arg-Gln-Gln-Gly-Glu-Arg-Asn-Gln-Glu-Gln----Leu⁴⁴-NH2
            -Lys-Tyr-Leu-Glu-Ser-Leu-Ile-NH2
            -Arg-Leu-Leu-Gln-Gly-Leu-Val-NH2
            -Asp-Phe-Val-Gln-Trp-Leu-Met-Asn-Thr
```

HYPOTHALAMIC POLYPEPTIDES WITH ADENYLATE CYCLASE STIMULATING ACTIVITY

This invention was made with Government support under Grant No. DK 09094, awarded by the National Institutes of Health. The Government has certain rights in this invention.

TABLE OF CONTENTS

1. Field of the Invention
2. Background of the Invention
   2.1 Hypothalamic Hormones
3. Summary of the Invention
4. Brief Description of the Figures
5. Detailed Description of the Invention
   5.1 Isolation and Purification
   5.2 Homologies
   5.3 Biological Activity
   5.4 Therapeutic Compositions
6. Examples
   6.1 Extraction and Purification
   6.2 Sequence Analyses
   6.3 Bioassay of Adenylate Cyclase Stimulation
   6.4 Superfusion Method Using Rat Pituitary Cell Column
   6.5 Determination of Depressor Activity

1. FIELD OF THE INVENTION

The present invention relates to novel hypothalamic polypeptides. Specifically, the present invention relates to novel 27-38 residue polypeptides which are capable of stimulating adenylate cyclase activity in pituitary cells, and to cause release of a number of hormones from such cells.

2. BACKGROUND OF THE INVENTION

2.1. Hypothalamic Hormones

A neuroendocrine pathway by which the central nervous system communicates with the anterior pituitary is by way of the hypothalamic-hypophyseal portal systems. A number of small peptide (i.e., 3-44 amino acids) hormones, known as hypophysiotropic hormones are produced by cells of the hypothalamus in extremely small amounts. Each of these hormones has a different specific function, but overall, most are stimulatory to certain cells of the pituitary, which cause the release of specific anterior pituitary hormones. Among the well-known hypophysiotropic hormones, corticotropic releasing hormones stimulates release of adrenocorticotropic hormone (ACTH) and β-endorphin; gonadotropin-releasing hormone (GnRH; also known as luteinizing hormone releasing hormone, LHRH) stimulates secretion of luteinizing hormone (LH) and follicle stimulating hormone (FSH); growth hormone releasing hormone (GHRH) stimulates growth hormone secretion; and thyrotropin releasing hormone (TRH) stimulates release of thyroid stimulating hormone (TSH) and prolactin. Some of these hypophysiotropic factors, however, are actually inhibitory; for example, somatotropin release inhibiting factor (somatostatin) inhibits secretion of growth hormone and TSH, and dopamine (a catecholamine) inhibits prolactin secretion.

A number of less well characterized, but apparently related "hormones" have also been described, many of which are associated with the digestive glands rather than the hypothalamus. One group of such peptides is the secretin-glucagon family of which vasoactive intestinal peptide (VIP) is a member. This family includes several well-known compounds such as GHRH, secretin, and glucagon, the activities of which have been very clearly characterized. VIP was originally isolated from the digestive tract, and has demonstrated activity in lowering blood pressure, but its role in day-to-day metabolism is still not clear.

ADENYLATE CYCLASE AND CYCLIC AMP

On a molecular level, the action of many peptide hormones is mediated by cyclic adenosine monophosphate (cyclic AMP or cAMP). In general terms, the hormone will bind to a receptor at the target cell's surface; this interaction between receptor and hormone stimulates production of cAMP from ATP by the action of adenylate cyclase, which is found on the internal surface of the cell membrane. The role of cAMP is to activate the enzyme protein kinase A. The cAMP which forms because of the receptor-hormone becomes bound reversibly to the regulatory subunit of the enzyme which in turn permits the catalytic subunit of the enzyme to act. The ultimate effect of the activity of protein kinase A is to catalyze transfer of a phosphate group from ATP to serine hydroxyl groups or other enzymes, which has the effect of either increasing or decreasing their activity. This alteration leads to the physiological effects which characterize the specific hormone's activity.

As can be seen from the above discussion, the ability to stimulate adenylate cyclase activity in vitro is a strong indicator of utility of a compound in regulating hormonally-controlled physiological events in vivo. The VIP family of peptides and all known hypothalamic releasing hormones have this activity, to a greater or lesser extent, although stimulation of adenylate cyclase may not always be an obligatory process for the action of these releasing hormones. It has now been discovered that a new series of peptides, one of which has been originally isolated from sheep hypothalamus, are potent stimulators of adenylate cyclase activity, as tested in rat pituitary cell cultures, having a stimulating effect of up to 100 to 1000 times that of VIP. As such, these compounds are useful in both in vitro and in vivo applications in which the enhancement of adenylate cyclase activity is desirable.

3. SUMMARY OF THE INVENTION

The present invention relates to novel peptides comprising the formula

His—Ser—Asp—Gly—Ile—Phe—Thr—Asp—Ser—Tyr—Ser—Arg—Tyr—Arg—Lys—Gln—Met—Ala—Val—Lys—Lys—Tyr—Leu—Ala—Ala—Val—Leu— and physiologically active analogues thereof. More specifically, a series of peptides, based on this formula, containing up to 38 amino acid residues have been shown to have biological activity of substantial therapeutic interest. Among the peptides in this category are the following:

1. His-Ser-Asp-Gly-Ile-Phe-Thr-Asp-Ser-Tyr-Ser-Arg-Tyr-Arg-Lys-Gln-Met-Ala-Val-Lys-Lys-Tyr-Leu-Ala-Ala-Val-Leu-Gly.
2. His-Ser-Asp-Gly-Ile-Phe-Thr-Asp-Ser-Tyr-Ser-Arg-Tyr-Arg-Lys-Gln-Met-Ala-Val-Lys-Lys-Tyr-Leu-Ala-Ala-Val-Leu-Gly-Lys.
3. His-Ser-Asp-Gly-Ile-Phe-Thr-Asp-Ser-Tyr-Ser-Arg-Tyr-Arg-Lys-Gln-Met-Ala-Val-Lys-Lys-Tyr-Leu-Ala-Ala-Val-Leu-Gly-Lys-Arg.
4. His-Ser-Asp-Gly-Ile-Phe-Thr-Asp-Ser-Tyr-Ser-Arg-Tyr-Arg-Lys-Gln-Met-Ala-Val-Lys-Lys-Tyr-Leu-Ala-Ala-Val-Leu-Gly-Lys-Arg-Tyr.
5. His-Ser-Asp-Gly-Ile-Phe-Thr-Asp-Ser-Tyr-Ser-Arg-Tyr-Arg-Lys-Gln-Met-Ala-Val-Lys-Lys-Tyr-Leu-Ala-Ala-Val-Leu-Gly-Lys-Arg-Tyr-Lys.
6. His-Ser-Asp-Gly-Ile-Phe-Thr-Asp-Ser-Tyr-Ser-Arg-Tyr-Arg-Lys-Gln-Met-Ala-Val-Lys-Lys-Tyr-Leu-Ala-Ala-Val-Leu-Gly-Lys-Arg-Tyr-Lys-Gln.
7. His-Ser-Asp-Gly-Ile-Phe-Thr-Asp-Ser-Tyr-Ser-Arg-Tyr-Arg-Lys-Gln-Met-Ala-Val-Lys-Lys-Tyr-Leu-Ala-Ala-Val-Leu-Gly-Lys-Arg-Tyr-Lys-Gln-Arg.
8. His-Ser-Asp-Gly-Ile-Phe-Thr-Asp-Ser-Tyr-Ser-Arg-Tyr-Arg-Lys-Gln-Met-Ala-Val-Lys-Lys-Tyr-Leu-Ala-Ala-Val-Leu-Gly-Lys-Arg-Tyr-Lys-Gln-Arg-Val.
9. His-Ser-Asp-Gly-Ile-Phe-Thr-Asp-Ser-Tyr-Ser-Arg-Tyr-Arg-Lys-Gln-Met-Ala-Val-Lys-Lys-Tyr-Leu-Ala-Ala-Val-Leu-Gly-Lys-Arg-Tyr-Lys-Gln-Arg-Val-Lys.
10. His-Ser-Asp-Gly-Ile-Phe-Thr-Asp-Ser-Tyr-Ser-Arg-Tyr-Arg-Lys-Gln-Met-Ala-Val-Lys-Lys-Tyr-Leu-Ala-Ala-Val-Leu-Gly-Lys-Arg-Tyr-Lys-Gln-Arg-Val-Lys-Asn.
11. His-Ser-Asp-Gly-Ile-Phe-Thr-Asp-Ser-Tyr-Ser-Arg-Tyr-Arg-Lys-Gln-Met-Ala-Val-Lys-Lys-Tyr-Leu-Ala-Ala-Val-Leu-Gly-Lys-Arg-Tyr-Lys-Gln-Arg-Val-Lys-Asn-Lys.

The useful peptides also encompass these sequences which are amidated at the carboxy terminus. Also included are biologically active analogues of these peptides, i.e., those derivatives of the claimed peptides which retain the stimulatory activity of the parent compound. For convenience of reference, these peptides are referred to throughout the following specification as Pituitary Adenylate Cyclase Activating Polypeptide or PACAP.

In effective amounts, the peptides of the present invention are potent activators of adenylate cyclase activity. The invention thus also provides a method for stimulating adenylate cyclase activity in vertebrate cells which comprises contacting the cells with an effective amount of a peptide of the present invention. Also provided are pharmaceutical compositions comprising a peptide of the present invention, in combination with a pharmaceutically acceptable carrier.

4. BRIEF DESCRIPTION OF THE FIGURES

FIG. 2a. Cation exchange chromatography of fr. 74–80 with ACSA obtained by Sephadex G-50 gel-filtration. Sample: lyophilized fractions 74–80 of the gel filtration. Column: Whatman CM-52, 1×20 cm. Fraction size: 4 ml/tube. Flow rate: 8 ml/hr. Solvent system: liner gradient elution from (A) to (B); (A) 10 mM ammonium formate (pH 6.5): $CH_3CN=90:10$ (v/v) (B) 0.8M Ammonium formate (pH 6.5): $CH_3CN=90:10$. Cyclic AMP levels (●) accumulated in the rat pituitary cell culture media after 3-hr incubation were used as the response parameter of ACSA. An open box shows the most potent ACSA (fr. 70–77) which was processed to present purification of PACAP38. Purification of other ACSA portions are in progress now.

FIG. 2c. Final purification of PACAP by RP HPLC. Sample: The ACSA fraction [A-II] eluted at 35–36 min on previous RP HPLC. Flow rate: 1.0 ml/min. Column: Vydac phenyl (4.6×250 mm). Solvent system: Linear gradient elution from (A) to (B) for 120 min; (A) $H_2O:CH_3CN:10\%TFA=90:10:1$ (v/v) (B) $H_2O:CH_3CN:10\%TFA=40:60:1$ (v/v). The ACSA fraction (I) was also purified under the same condition.

FIG. 6. Rat neurons, astrocytes and pituitary cells were examined for intracellular accumulation in vitro after addition of synthetic PACAP38, PACAP27NH2, CRH and VIP.

5. DETAILED DESCRIPTION OF THE INVENTION

5.1. Isolation and Purification

The peptides of the present invention were discovered in an effort to identify heretofore unknown hypophysiotropic hormones or factors, from hypothalamus. Sheep hypothalamic extracts were screeened for adenylate cyclase stimulating activation (ACSA) activity in rat pituitary cell cultures. Although ACSA activity is not always obligatory for the activity of hypothalamic releasing hormones, all known hormones of this type have been shown to stimulate adenylate cyclase in pituitary cells; this process is associated with a rise in cAMP in cells and culture medium. Even those hormones, such as LHRH and TRH which do not appear to require cAMP as a "second messenger", also increase cAMP in pituitary cell cultures. Therefore, this screen was utilized as an initial indicator of potential hormonal activity.

Figure 4:
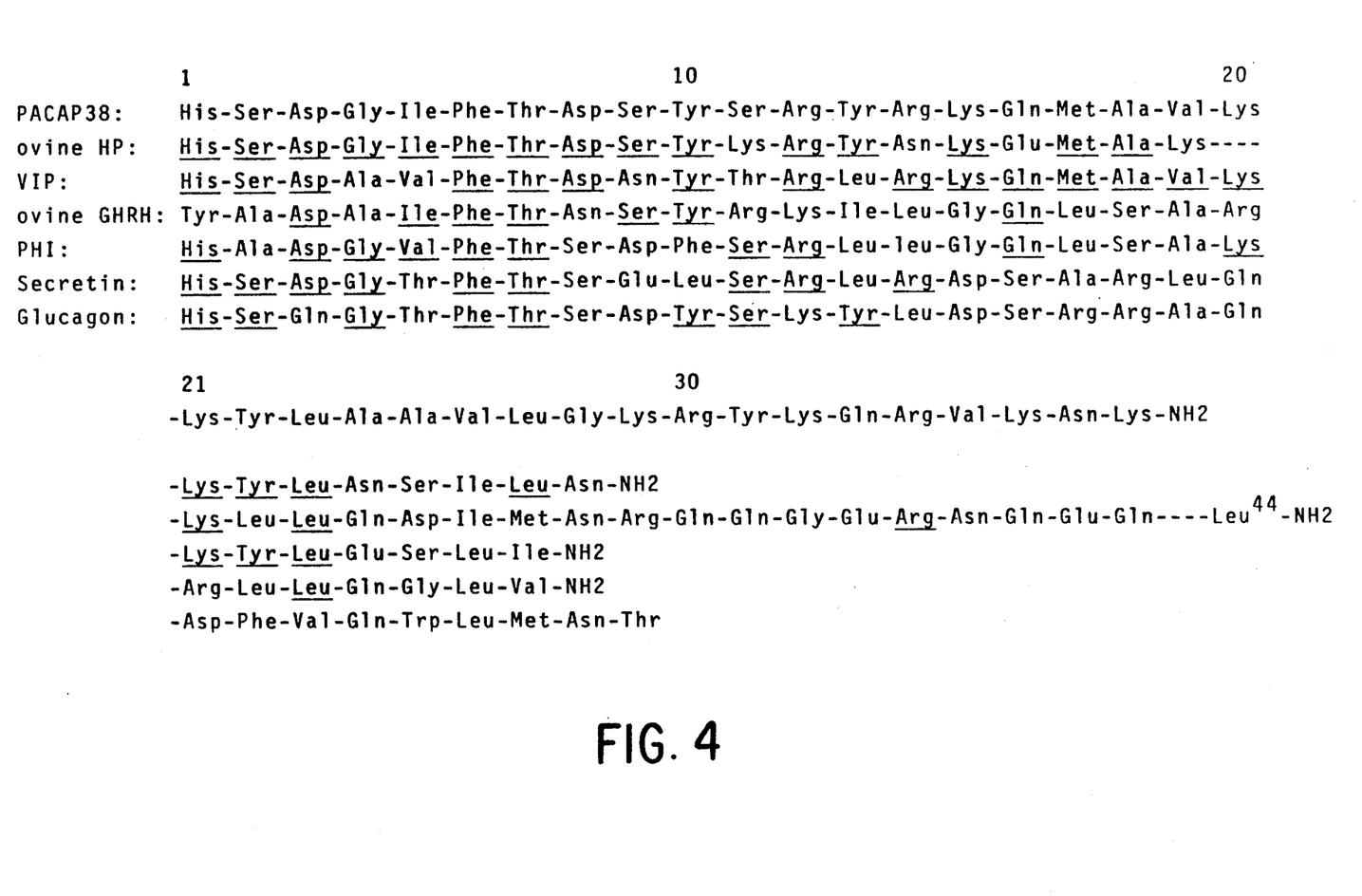
FIG. 4. Amino acid sequence of PACAP38 with related peptides: ovine HP, VIP, ovine GHRH, PHI, secretin, glucagon. Residues which are underlined indicate amino acid identities with PACAP38. The number at the top refers to amino acid number of the indicated peptide.
Figure 5A:
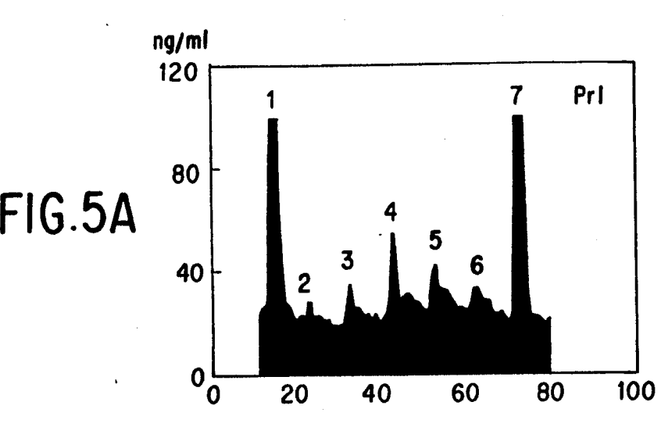
FIGS. 5A–5D. The effect of synthetic PACAP38 on the release of pituitary hormones from superfused pituitary cells. A pituitary cell superfusion method to determine the hypophysiotropic activity of samples was conducted as reported by Vigh and Schally. The peptide was applied as a 3 min pulse. The numbers at top indicate; 1,7: 100 mM KCl, 2: $10^{-10}$ M PACAP38, 3: $10^{-9}$ M PACAP38, 4: $10^{-8}$ M PACAP38, 5: $10^{-7}$ M PACAP38, 6: $10^{-6}$ M PACAP38. 0.9 ml fractions were collected every 3 min. Each fraction was determined for GH, Prl, ACTH, LH, FSH and TSH by RIA using the respective RIA kits provided by National Hormone and Pituitary Program, NIDDK.
Figure 5B:
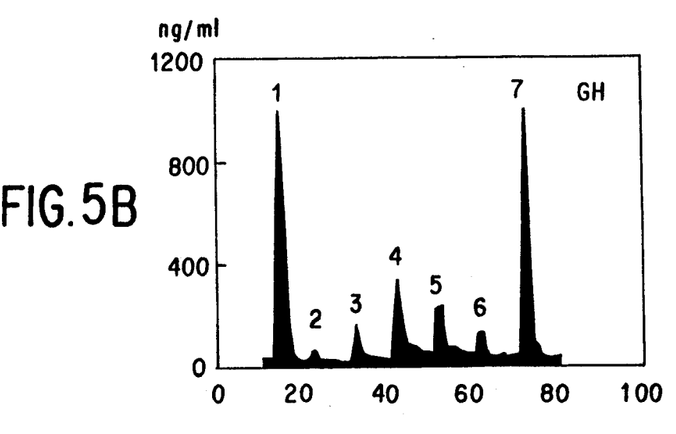
Figure 5C:
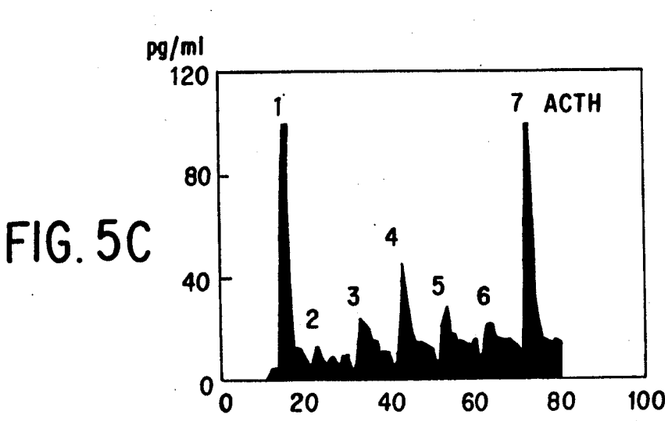
Figure 5D:
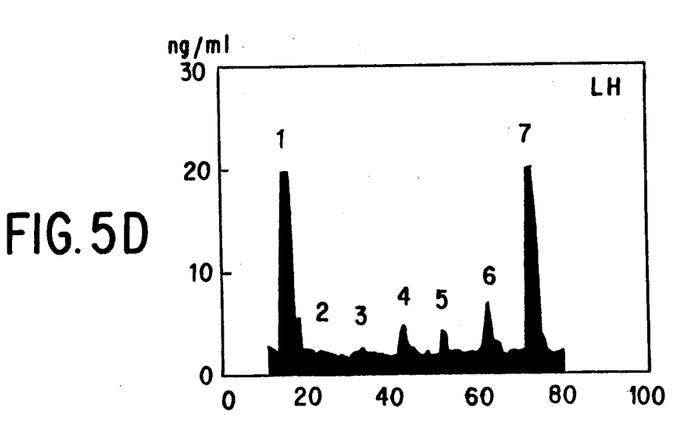

Fresh ovine hypothalamic tissue was boiled, and extracted, and treated with 66% acetone. The supernatant was absorbed on a C-18 column and eluted stepwise with 10, 20, 30, 40, 50, and 60% CH$_3$CN/0.1% TFA yielding fractions A, B, C, D, E and F, respectively. Fractions C and D which showed marked ACSA activity were separately loaded on a SP-Sephadex Column and eluted stepwise with 1M AcOH(SP-I), 2M pyridine (SP-II) and 2M pyridine acetate (SP-III). SP-III from both fractions C and D showed significant ACSA. Gel-filtration of Fraction D/SP-III yielded one major peak of ACSA, corresponding to a molecular weight of about 5000. The active fraction was purified, and found to be ovine GHRH. However, the gel-filtration of Fraction C/SP-III yielded a broad-peak of ACSA, corresponding to a molecular weight range of 1000–7000. Those fractions corresponding to a molecular weight of about 4000 were further purified. This led to the identification of a basic, 38-residue peptide, which has now been characterized and sequenced. The amino acid sequence of this peptide is shown in FIG. 4. The initial C-terminal analysis of this peptide was performed with carboxypeptidase B or Y digestion, followed by PTC amino acid analysis of released C-terminal amino acid with the PicoTag method (Waters), suggesting that the C-terminus of the peptide was amidated.

Based on the known amino acid sequence, two 38-residue peptides with this sequence, with either a free- or amidated C-terminus were synthesized by a solid phase method, and their retention times compared to that of the native PACAP38 peptide on RP HPLC. The native peptide coeluted with synthetic PACAP38-NH$_2$ and separated from PACAP38-OH. This confirmed that the C-terminus of the native peptide is amidated. However, when both synthetic peptides were compared with the native peptide, similar ACSA activity was shown (FIG. 2) for each. The first peak in the first RP HPLC or a TSKODS column was also purified and showed the same sequence as PACAP38. It was identified as [Met(o)$^{17}$]-PACAP38, indicated by the same retention time as synthetic PACAP38 after oxidation with performic acid on RP HPLC.

PACAP38 has three base pairs which are known to be processing sites of hormone precursors. In particular, the third paired basic residue at 28–29 is preceded by Gly, which is essential for C-terminal amidation by serving as a nitrogen donor to amidate the preceding residue. This structure is commonly found in the precursor of other C-terminal amidated hormones. Therefore, it was predicted that putative processing and amidation might yield PACAP27 NH$_2$. This peptide was also synthesized and found to possess similar, if not greater, ACSA activity than PACAP38 [FIG. 6]. The presence of PACAP27-NH$_2$ in native form in hypothalamic tissue remains to be verified.

5.2. Homologies

A computer-assisted search for homology of sequence of PACAP38 revealed that the N-terminal portion [1–28] has 68% homology with porcine and ovine vasoactive intestinal polypeptide (VIP). On the other hand, the sequence of the C-terminal region [29–38] showed no homology with any other known peptides. We have previously reported the isolation and partial structure of an ovine hypothalamic peptide (HP) which stimulated GH release from rat pituitary fragments in vitro (Arimura et al., Peptides 5, suppl. 1:41, 1984). The N-terminal amino acid sequence was: His-Ser-Asp-Gly-Ile-Phe-Thr-Asp-Ser-Tyr-Lys-Arg-Tyr-Asn-Lys-Glu-Met-Ala-Lys-. Due to the unavailability of a sufficient amount of ovine hypothalamic tissues, we could neither complete nor confirm the primary structure of this peptide. It is possible that PACAP38 is of the same family, or is of a very closely-related family, as this peptide. PACAP38 also shows a certain degree of homology with GHRH, peptide histidine isoleucine (PHI), secretin and glucagon, and seems to be a chimera of these peptides (FIG. 4). In any case, the sequence common to that of VIP, Arg-Lys-Gln-Met-Ala-Val-Lys-Lys-Tyr-Leu-, may reflect a distant ancestral relatedness between VIP and PACAP38.

5.3. Biological Activity

Because of the observed homology between PACAP38 and VIP, comparisons were made to determine what similarities, if any, may exist between the two peptides. In urethane-anaesthetized rats, both peptides showed comparable vasodepressor activity in a dose range between 0.33 nmole and 1.0 nmole. However, PACAP38 showed at least 100 times greater ACA than that of porcine VIP. Preliminary studies also indicate that the receptors for PACAP38 in rat pituitary membrane preparations are different from those of VIP, suggesting that PACAP38 may have a physiological role different from that of VIP.

PACAP has been shown to be capable of causing release of a number of hormones from superfused rat pituitary. Specifically, PACAP38 stimulated release of GH, PRL and ACTH in a dose dependent manner in a dose range between about M to $10^{-10}$ M to $10^{-8}$ M. Responses declined as the doses increased showing bell-shaped dose response curves for these hormones (FIG. 5). However, LH response was linear in a dose range of $10^{-9}$ to $10^{-6}$ M (FIG. 5). FSH and TSH release was not altered under the same conditions.

The ability of PACAP to stimulate cAMP production, both in terms of intracellular accumulation and extracellular production was evaluated in a number of different cell types, including neurons, pituitary cells and astrocytes.

Figure 3:
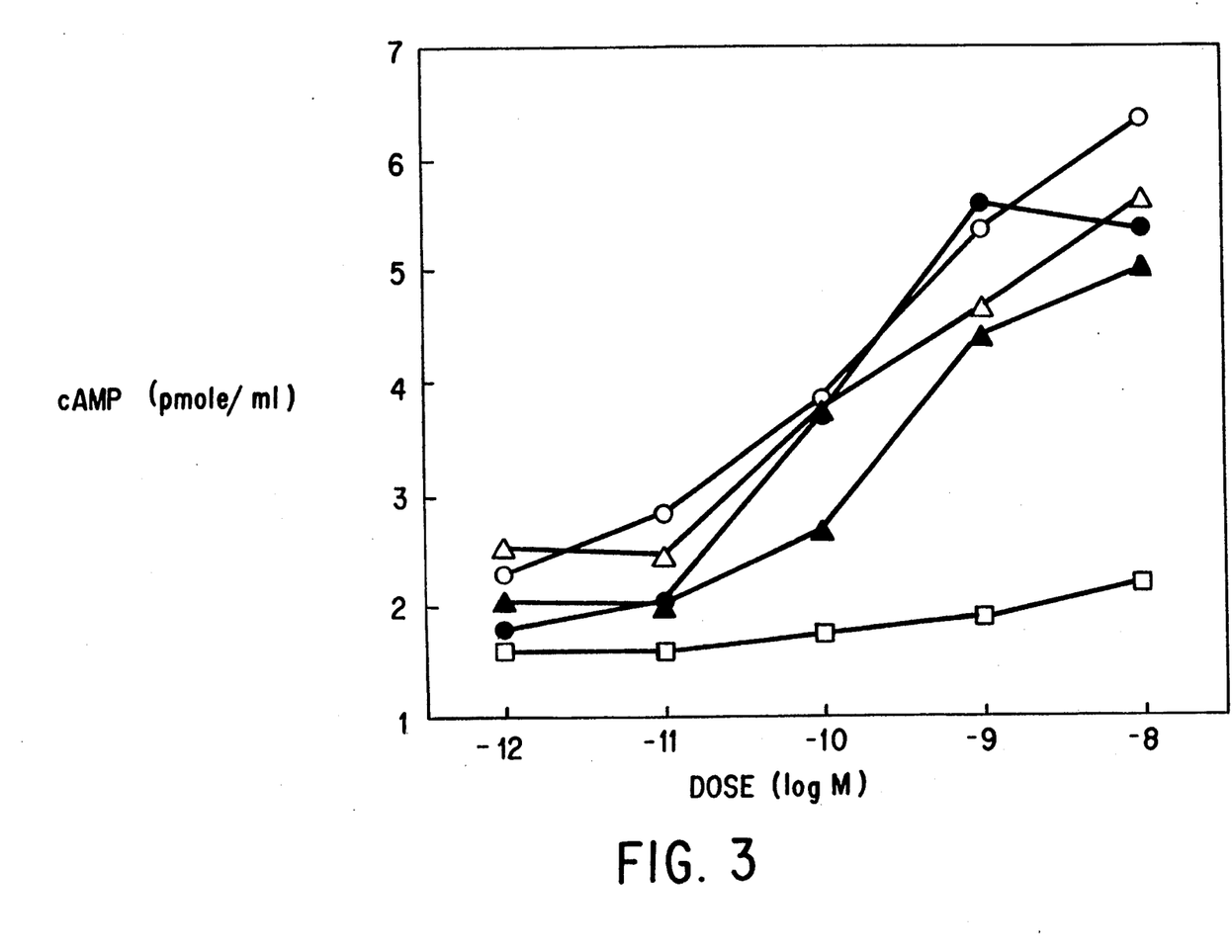
FIG. 3. ACSA of purified native ovine PACAP38 (○), synthetic PACAP38NH2 (●), and synthetic PACAP38OH (△) as compared with VIP (□) and CRH (▲) determined using rat pituitary cell cultures.
Figure 7:
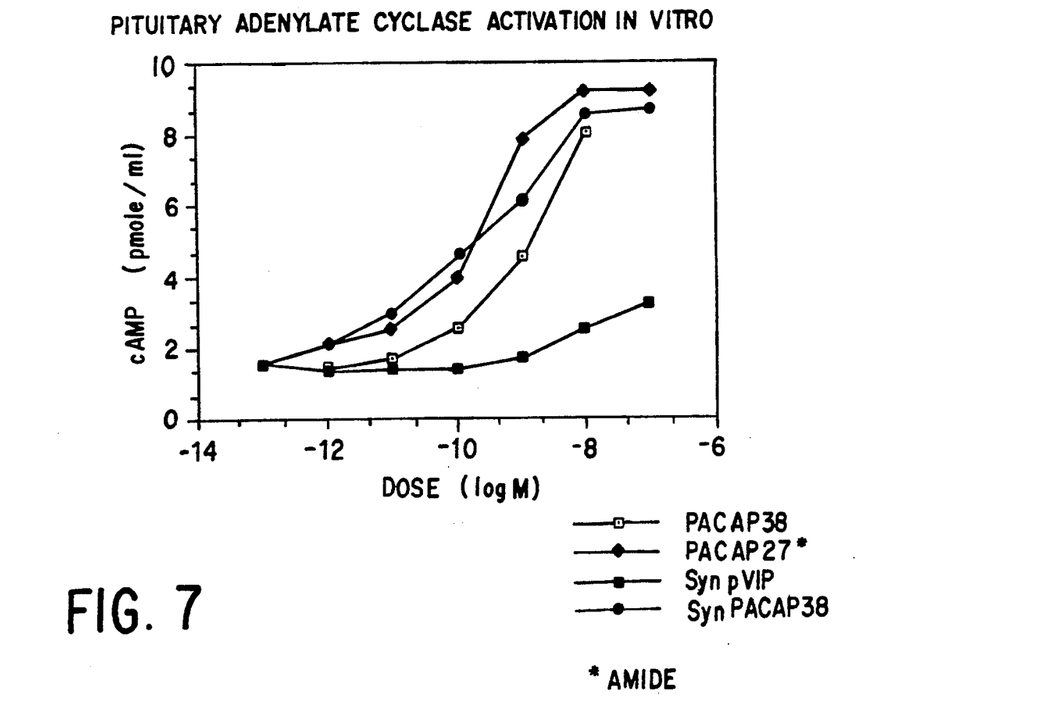
FIG. 7. Extracellular secretion of cAMP was measured in vitro for native PACAP38, synthetic PACAP27NH$_2$, synthetic VIP and synthetic PACAP38.

FIG. 7 shows data plotting the increase in extracellular cAMP in the rat pituitary cell cultures by PACAP38, PACAP27NH$_2$, AND pVIP. We also determined temporal changes in intracellular cAMP levels in rat pituitary cell cultures. As shown in FIG. 3, PACAP38, PACAP27NH$_2$, and CRH induced a comparable extent and pattern of cAMP accumulation. GRH induced the greatest accumulation of intracellular cAMP. On the other hand, pVIP showed little effect at this concentration.

For studies on neurons, rat neuronal cell cultures were prepared by the method described by Raizada et al. (Raizada et al. *Am. J. Physiol.* 247:C364, 1984). Astrocyte cultures were prepared using the single-step transfer method as described by Clarke et al. (Clark et al., *J. Biol. Chem.* 259:11672, 1984). The addition of PACAP38 at a dose of $10^{-9}$ M to the culture medium increased intracellular cAMP in both neurons and astrocytes. However, the response of astrocytes was extraordinarily large (FIG. 6b) as compared to the response of neurons (FIG. 6c). Cyclic AMP increased as early as one minute after addition of PACAP38. Intracellular cAMP levels remained elevated for at least 60 minutes in astrocytes, but began to decrease after 10 min in neurons. Porcine VIP in a dose of $10^{-9}$ M did not induce an appreciable stimulation of cAMP either in neuron or astrocyte cell cultures.

5.4. Therapeutic Compositions

The observed biological activities of the PACAP peptides indicate significant therapeutic potential. Of particular interest is the prevention of neuronal cell death which may be associated with a number of physiological conditions, such as AIDS infection, or mechanical damage to the brain. It has been previously noted that VIP, a peptide with significant homology to PACAP, is capable of protecting neurons from cell death induced by the gp120 envelope glycoprotein of the AIDS virus (De Brenneman et al., *J. Cell Biol.* 104:1603–1610, 1987; De Brenneman et al. *Nature* 335:639–642, 1988). Given the structural similarity between PACAP and VIP, and the greater level of activity shown by PACAP, it is expected that PACAP will have a greater capacity for prevention of neuronal cell death.

Suitable pharmaceutical compositions can be prepared by incorporation of an effective amount of the peptide in combination with a pharmaceutically acceptable carrier. For parenteral administration, the carrier may be any appropriate vehicle, such as physiological saline or a physiologically acceptable buffer. The peptide can be also combined with suitable binders or extenders for administration orally. The methods and components of such compositions are well known in the art.

6. EXAMPLES

6.1. Extraction and Purification

Three thousand (3000) ovine hypothalami were collected and kept frozen at $-70°$ C. until extraction. Tissue (2400 g) was boiled for 10 min in 10 volumes of water to inactivate intrinsic proteases. After cooling over ice, glacial acetic acid (AcOH) and $\beta$-mercaptoethanol ($\beta$-ME) were added to yield a final concentration of 2M and 0.02%, respectively, and were then homogenized with a Polytron at $4°$ C. The extract was centrifuged at 17,000$\times$g, and the supernatant was added to acetone to a final concentration of 66%. After removal of precipitates, the supernatant was evaporated in vacuo to dryness. Residual materials were dissolved in 0.5M AoOH and then placed on a Vydao C18 (20–30 $\mu$m) column (3$\times$13 cm), pre-equilibrated with 0.5M AcOH. Successive elution with step-wise increments of acetonitrile concentration of 10, 20, 30, 40, 50, and 60% in 0.1% TFA yielded six respective fractions: A, B, C, D, E, F. An aliquot of each fraction was evaporated to dryness and subjected to a bioassay for adenylate cyclase stimulating activation (ACSA) using rat pituitary cell cultures. Frs. C and D were found to be active. Fr. C was used as the starting material for purification. Fr. C dissolved in 1M AcOH was applied on to a column of SP Sephadex C-25 (H+ form), pre-equilibrated with 1M AcOH. Successive elution with 1M AcOH, 2M pyridine and 2M pyridine-AcOH (pH 5.0) yielded three respective fractions, SP-I, SP-II and SP-III. An aliquot of each fraction was assayed for ACSA. SP-III was found to have activity. The SP-III was then subjected to gel-filtration on a Sephadex G-50 (fine) column (5.5$\times$97 cm) using 2M AcOH/0.02% $\beta$-ME as the eluting buffer. Column effluents were monitored for O.D. at 280 nm. An aliquot of each fraction was subjected to bioassay. Fractions with ACSA activity were pooled and lyophilized. The residue was reconstituted with 10 mM ammonium formate (pH 6.5): CH$_3$CN$=$90:10 and absorbed on a column (1$\times$38 cm) of CM-52 Cellulose (Whatman), pre-equilibrated with 10 mM ammonium formate: CH$_3$CN$=$90:10. Chromatography was performed using a linear gradient of ammonium formate from 10 mM to 0.8M as described in the legend of FIG. 2. The bioactive portion purified by ion-exchange chromatography was then applied on a TSK ODS 120-T column (4.6$\times$250 mm) and eluted with a linear gradient of acetonitrile as described in the legend of FIG. 3. The active fraction was finally purified on a Vydac phenyl column (4.6$\times$250 mm). During HPLC, column effluents were monitored by measuring absorbance at 210 nm and 280 nm, simultaneously.

Basic peptide fractions (SP-III) obtained from C18 fractions C and D, prepared from the extract of ovine hypothalami, showed marked ACSA activity. Gel-filtration of Fr. D/SP-III yielded one potent peak of ACSA activity, corresponding to m.w. 5,000. The active fraction was purified to a pure form. Sequence analysis of the substance revealed that this active material was ovine GHRH[1–44]. This was additionally confirmed by radioimmunoassay for ovine GHRH.

Figure 1:
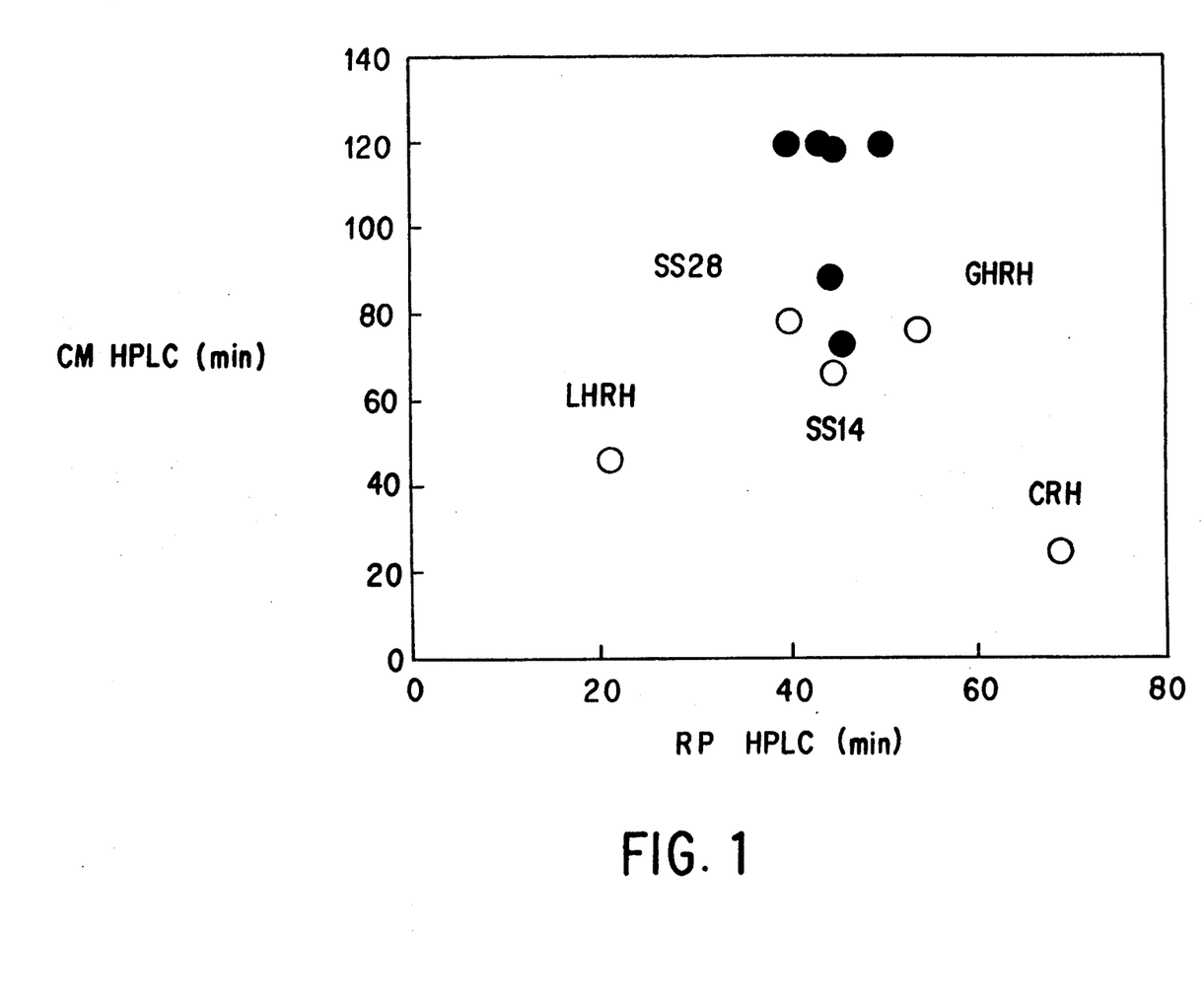
FIG. 1. The retention times on RP HPLC for Adenylate Cyclase Stimulating Activity (ACSA) which represent hydrophobicity were plotted on the abscissa, and those of IEX HPLC which represent electrical charge on the ordinate, thus creating a two-dimensional map for hydrophobicity and electrical charge of each active fraction RP HPLC was performed on a TSK ODS 120T column under the same elution condition as described in FIG. 2b legend. IEX HPLC was performed on a TSK 2SW column in a gradient of ammonium formate (pH 6.5) 10 mM to 0.5M for 100 m in, then increased to 1.0M for 20 min. Various known hypothalamic releasing hormones (RHs) (○) were also subjected to RP HPLC and IEX HPLC under the same condition and mapped to show the presence of any novel hypothalamic substances (●) in locations different from those of known RHs. Each activity was also subjected to GHRH and CRH RIAs.
Figure 2A:
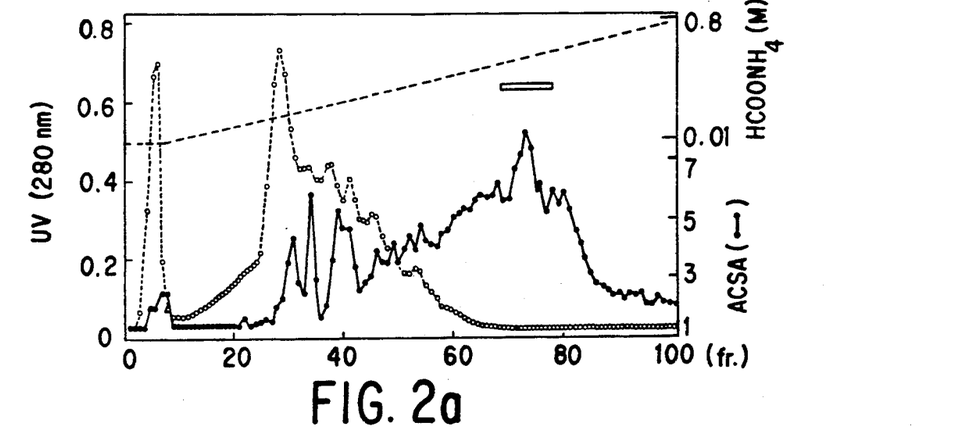
Figure 2B:
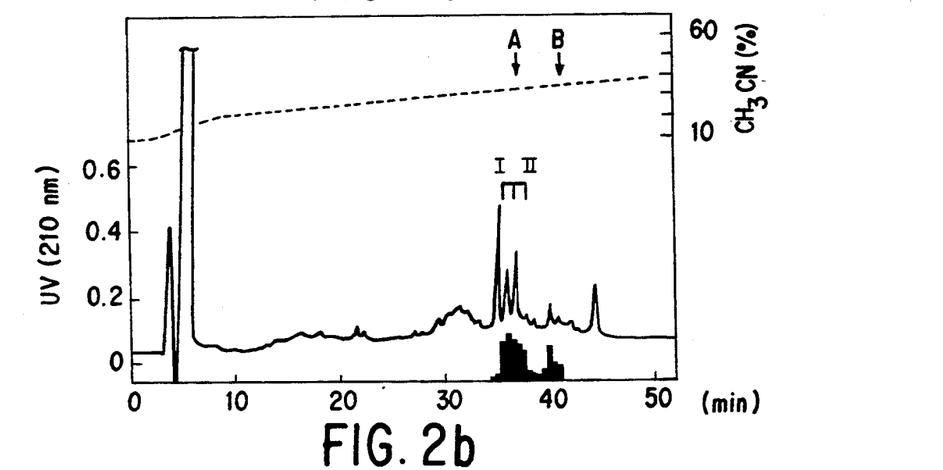
FIG. 2b. Reverse phase HPLC of ion exchange chromatography fraction with ACSA. Sample: The ACSA active fraction eluted at fr. 70–77. Flow rate: 1.0 ml/min. Column: TSK ODS 120T (4.6×250 mm, ToyoSoda). Solvent system: Linear gradient elution from (A) to (B) for 120 min; (A) $H_2O:CH_3CN=10\%TFA=90:10:1$ (v/v) (B) $H_2O:CH_3CN:10\%TRA=40:60:1$ (v/v). The black bar shows the ACSA (A and B). The major ACSA portions (a) were divided into I, 34–35 min, and II, 35–36 min, corresponding to the respective UV absorbance peaks.
Figure 2C:
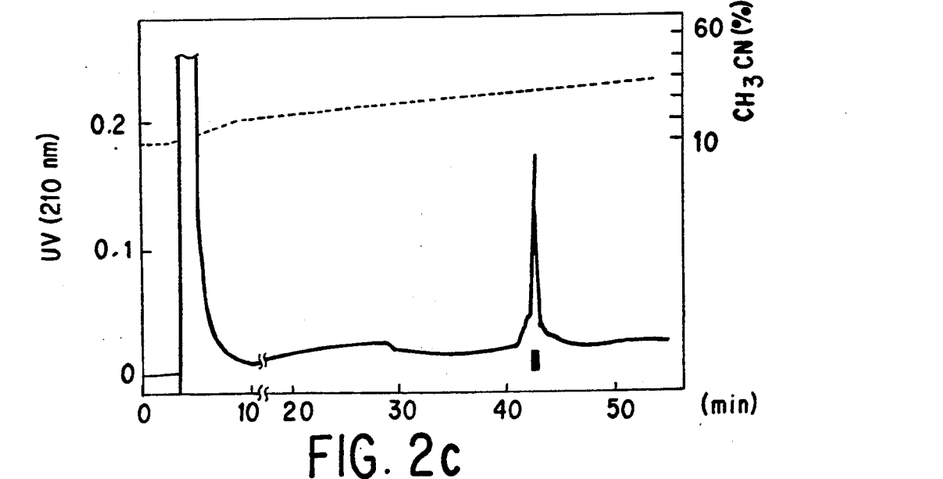

On the other hand, gel-filtration of Fr. C/SP-III yielded a broad peak of ACSA activity, corresponding to m.w. ranging from 1,000 to 7,000. Fractions corresponding to m.w. ca. 3,000–4,000 were pooled and lyophilized, and then further purified by ion exchange HPLC. As shown in FIG. 2a, one major peak and 7 minor peaks of ACSA activity emerged on the chromatogram and the major activity (fr. 70–77) was isolated. Three peaks of ACSA activity, eluted at fr. 28–43, showed GHRH-like immunoactivity as indicated by RIA. Purification of other peaks with ACSA activity is in progress. The ACSA activity of the major peak (fr. 70–77) was further purified by reverse phase HPLC on a TSK ODS 120T column. The ACSA activity then separated into two peaks, one large and one small (FIG. 2b). Two sharp UV peaks merged in the area of the major ACSA peak previously shown. These two UV peak fractions were separately purified by another reverse phase HPLC on a Vydac phenyl column (FIG. 2c). Each yielded a symmetric UV peak which eluted at 41 min and 43 min, respectively. Each was subjected to sequential analysis and showed an identical amino acid sequence. It was found that the earlier eluted peak represented the oxidized form and the later, the reduced form. The purity of each peptide was also confirmed by another reverse phase HPLC system.

6.2. Sequence Analyses

Because of the very small amount of the peptide, all analyses were carried out on a subnanomole scale. One-sixth of the highly purified peptide with ACSA activity (ca. 100 pmole) was applied directly to the automated protein/peptide sequencer (Applied Biosystems, Model 477A), coupled with HPLC identification of resulting amino acids by PTH 120A Analyser. The operation of the sequencer is based on the sequential degradation chemistry of Pehr Edman. The PTH Analyser uses gradient microbore chromatography to separate and detect the products of this degradation. The sequencer controller collects and analyzes chromatographic data to interpret the sequence information. The carboxy terminal analysis of PACAP [1–38] was carried out by digesting with carboxypeptidase Y and B (Sigma Chemical Co., St. Louis, Mo.; 100 ng each) in 10 $\mu$l of 0.1M ammonium bicarbonate (pH 8.0) at 37° C. After 1 h incubation, analysis of released amino acids was performed at the picomole level using a pre-labeling analysis system (Waters, Pico-Tag). The picotag method utilizes phenylisothiocyanate (PITC) as a tagging reagent in the precolumn derivatization of amino acids. A one-step reaction between amino acids and PITC yields stable phenylthiocarbamate (PTC) amino acids derivatives, each containing a UV-active chromophore for both primary and secondary amino acids. The resulting PTC amino acids are then separated on reverse phase HPLC.

6.3. Bioassay of Adenylate Cyclase Stimulation

Primary monolayer rat anterior pituitary cell culture was prepared as described previously (Culler et al., 1984). Anterior pituitaries from CD strain female rats of approximately 200 g bw (Charles River Breeding Labs, Wilmington, Mass.) at a random stage of estrous cycle were enzymatically dispersed with collagenase Type II and DNAse II. Dispersed cells were collected by centrifugation and washed three times with HEPES buffer and finally suspended in Dulbecco,s modified Eagle's medium (DMEM) containing 10% horse serum, 2.5% fetal calf serum and 1% antibiotic antimycotic solution (Gibco/Life Technologies, Grand Isle, NY) The cells are plated in 24-multiwell tissue culture plates (Falcon, Oxnard, Calif.) at a density of $1.5 \times 10^5$ cells/ml/well, and then incubated at 37° C. in a water-saturated atmosphere of 95% air 5% $CO_2$ for 4 days. Prior to acute stimulation, cultured cells were incubated for 3 hr in serum-free DMEM with two changes of the medium. The cells were then incubated for 3 hr in 0.5 ml of HEPES-buffered DMEM containing test materials. Ascorbic acid ($2.5 \times 10^{-4}$ M) and 0.25% BSA were routinely added to the medium during assay incubation in order to prevent possible oxidation and adsorption of test samples. At the end of each test incubation period, medium was collected separately from each well and stored at $-70°$ C. until assayed for cAMP and pituitary hormones of interest by their respective radioimmunoassays (RIAs).

Cyclic AMP in the culture media was determined by RIA as described by Harper and Brooker (J. Cyclic Nucleo. Res. 1:207, 1975). Samples and the standards in 500 $\mu$l were acetylated by adding 15 $\mu$l of a mixture of triethylamine and acetic anhydride (2:1). The antiserum against cAMP was generated by Dr. Makoto Tamura and Tyr-AMP for iodination was a gift from Yamasa Corp., Japan. Tyr-AMP was iodinated by $^{125}I$ using the lactoperoxidase method and purified by HPLC. In our hands, the cAMP RIA could detect as small an amount as 1 fmole/tube. The determination of pituitary hormones in the medium was also made by RIA using the respective RIA kits provided by National Pituitary Hormone Program, NIDDK.

Figure 6A:
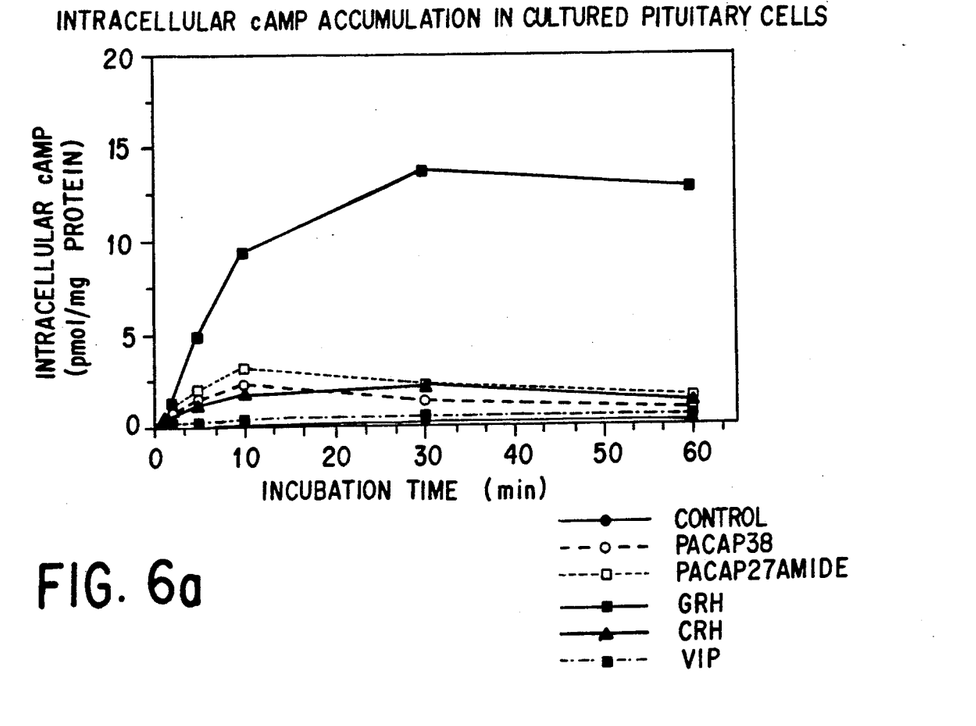
FIG. 6a. Intracellular cAMP accumulation in cultured pituitary cells.
Figure 6B:
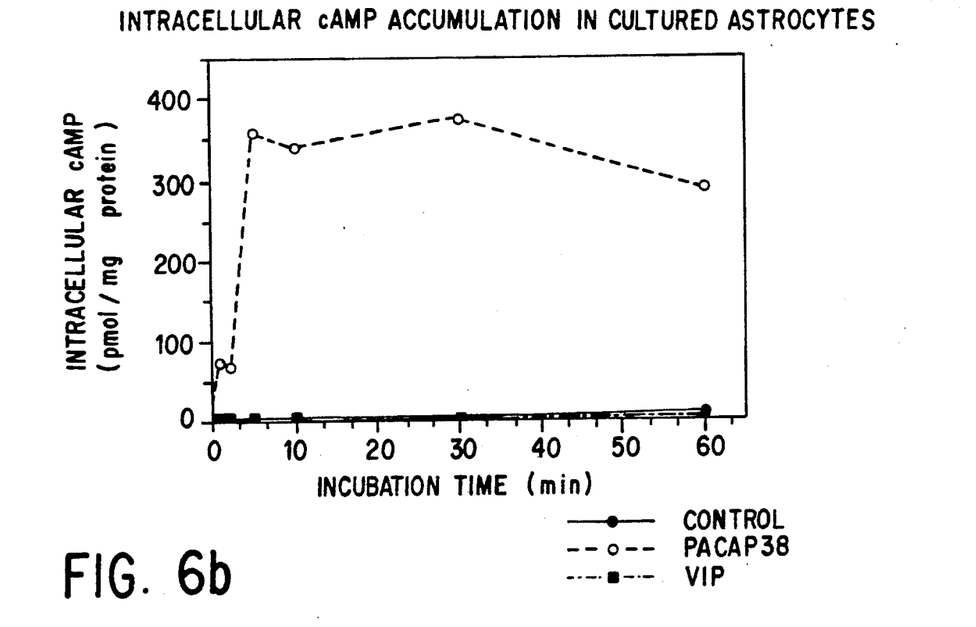
FIG. 6b. Intracellular cAMP accumulation in cultured astrocytes.
Figure 6C:
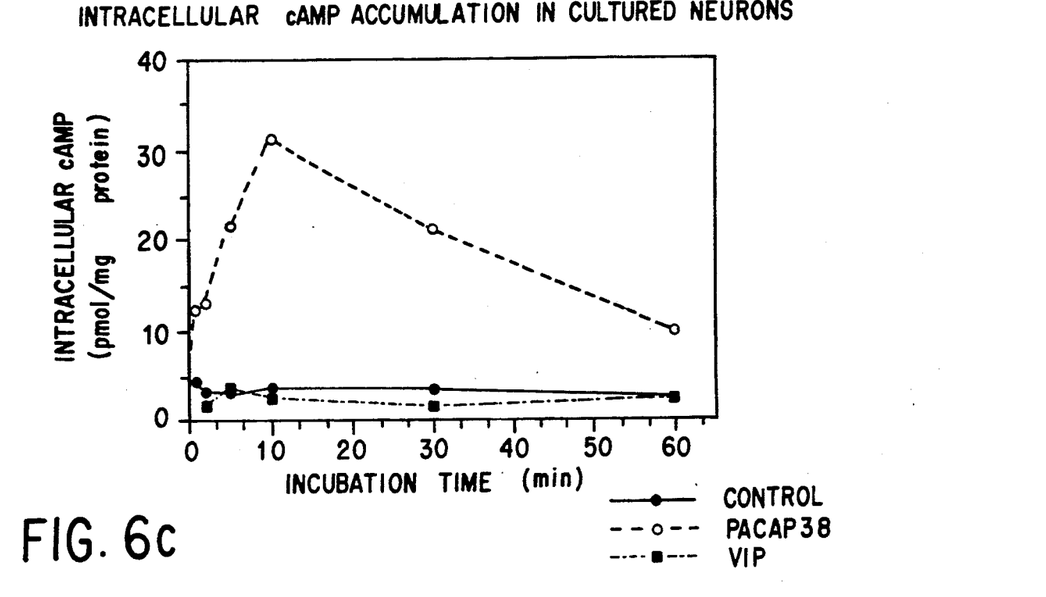
FIG. 6c. Intracellular cAMP accumulation in cultured neurons.

Data on the production of both extracellular cAMP as well as intracellular accumulation of cAMP is shown in FIGS. 5 and 6, respectively.

6.4. Superfusion Method Using Rat Pituitary Cell Column

A pituitary cell superfusion method to determine the hypophysiotropic activity of samples was conducted as reported by Vigh and Schally (1984). Pituitaries obtained from 3 adult female rats were cut into small pieces and incubated in a Dubnoff incubator for 45 min at 37° C. in 10 ml of oxygenated Medium 199 (Gibco/Life Technologies) containing 0.5% collagenase (Sigma Type I), 0.25% BSA and 50 $\mu$l/ml gentamicin sulphate (Sigma). After this incubation, there were no apparent changes in the pituitary tissue, but the fragments could be easily dispersed into single cells by repeated suction and expulsion from a Pasteur pipet. After 30 to 60 pipet operations, the tissue fell apart. The cell suspension was centrifuged at room temperature for 10 min at $100 \times g$. The cell pellet was then resuspended in 1.0 ml medium. A small aliquot was diluted to count the cells, and the remainder of the suspension was divided into 2 equal volumes. Each volume (containing about $5 \times 10^6$ cells and usually between 3.5 and $7.0 \times 10^6$) was mixed with 0.5 ml Sephadex G-15 which had been equilibrated with previously oxygenated medium. The mixture of pituitary cells and Sephadex was transferred into 2 chambers of the superfusion apparatus and perfused with the medium. The medium was always freshly prepared in a way similar to that for enzymatic dispersion, omitting the collagenase, then passed through a Millipore filter, and continuously gassed with a mixture of $O_2$ (95%) and $CO_2$ (5%) during the experiment. The flow rate of the medium through the superfusion system was controlled by a multichannel pump (Gilson Minipulse Type HP-8) which was placed behind the superfusion chamber; the tuning of the lower plunger was connected to the pump, and from there to a two-channel fraction collector. Thus, the system was operated with negative pressure in order to get fewer fluctuations in the flow rate. Samples were applied as a 3 min pulse followed by the medium superfusion. Superfusate was collected as 3 min fractions, 0.9 ml per fraction.

6.5. Determination of Depressor Activity

Arterial blood pressure was measured in urethane (150 mg/100 g ip) anesthetized adult male rats. Polyethylene tubing (PE50) which was connected with a pressure transducer P-1000 B (Narco Bio-Systems) was inserted into the femoral artery. Blood pressure was recorded using Narcotrace 40. Another polyethylene tube (PE50) was inserted into a femoral vein for injection of test materials dissolved in 0.5 ml 0.9% saline.

Since VIP induces relaxation of the smooth muscle of blood vessels and lowers blood pressure, PACAP, which has a structure homologous to VIP, was examined for depressor activity. PACAP27NH$_2$ and porcine VIP demonstrated a similar depressor activity in anesthetized rats. PACAP38 also showed a significant, but somewhat weaker, depressor activity than PACAP27NH$_2$. As shown in FIG. 5, the peptide stimulated release of prolactin (PRL), growth hormone (GH), adrenocorticotropic hormone (ACTH), and luteinizing hormone (LH). PACAP38 exhibited a bell-shaped, dose response curve with its maximum effect at $10^{-8}$ M. The minimum effective dose was $10^{-10}$ M. The peptide induced a dose-related LH relese in a range between $10^{-10}$ M and $10^{-6}$ M. Its effect on TSH and FSH release was not apparent.

What we claim is:

1. A peptide consisting of peptides selected from the group of peptides having the following formulas:

His-Ser-Asp-Gly-Ile-Phe-Thr-Asp-Ser-Tyr-Ser-Arg-Tyr-Arg-Lys-Gln-Met-Ala-Val-Lys-Lys-Tyr-Leu-Ala-Ala-Val-Leu;

His-Ser-Asp-Gly-Ile-Phe-Thr-Asp-Ser-Tyr-Ser-Arg-Tyr-Arg-Lys-Gln-Met-Ala-Val-Lys-Lys-Tyr-Leu-Ala-Ala-Val-Leu-Gly;

His-Ser-Asp-Gly-Ile-Phe-Thr-Asp-Ser-Tyr-Ser-Arg-Tyr-Arg-Lys-Gln-Met-Ala-Val-Lys-Lys-Tyr-Leu-Ala-Ala-Val-Leu-Gly-Lys;

His-Ser-Asp-Gly-Ile-Phe-Thr-Asp-Ser-Tyr-Ser-Arg-Tyr-Arg-Lys-Gln-Met-Ala-Val-Lys-Lys-Tyr-Leu-Ala-Ala-Val-Leu-Gly-Lys-Arg;

His-Ser-Asp-Gly-Ile-Phe-Thr-Asp-Ser-Tyr-Ser-Arg-Tyr-Arg-Lys-Gln-Met-Ala-Val-Lys-Lys-Tyr-Leu-Ala-Ala-Val-Leu-Gly-Lys-Arg-Tyr;

His-Ser-Asp-Gly-Ile-Phe-Thr-Asp-Ser-Tyr-Ser-Arg-Tyr-Arg-Lys-Gln-Met-Ala-Val-Lys-Lys-Tyr-Leu-Ala-Ala-Val-Leu-Gly-Lys-Arg-Tyr-Lys;

His-Ser-Asp-Gly-Ile-Phe-Thr-Asp-Ser-Tyr-Ser-Arg-Tyr-Arg-Lys-Gln-Met-Ala-Val-Lys-Lys-Tyr-Leu-Ala-Ala-Val-Leu-Gly-Lys-Arg-Tyr-Lys-Gln;

His-Ser-Asp-Gly-Ile-Phe-Thr-Asp-Ser-Tyr-Ser-Arg-Tyr-Arg-Lys-Gln-Met-Ala-Val-Lys-Lys-Tyr-Leu-Ala-Ala-Val-Leu-Gly-Lys-Arg-Tyr-Lys-Gln-Arg;

His-Ser-Asp-Gly-Ile-Phe-Thr-Asp-Ser-Tyr-Ser-Arg-Tyr-Arg-Lys-Gln-Met-Ala-Val-Lys-Lys-Tyr-Leu-Ala-Ala-Val-Leu-Gly-Lys-Arg-Tyr-Lys-Gln-Arg-Val;

His-Ser-Asp-Gly-Ile-Phe-Thr-Asp-Ser-Tyr-Ser-Arg-Tyr-Arg-Lys-Gln-Met-Ala-Val-Lys-Lys-Tyr-Leu-Ala-Ala-Val-Leu-Gly-Lys-Arg-Tyr-Lys-Gln-Arg-Val-Lys;

His-Ser-Asp-Gly-Ile-Phe-Thr-Asp-Ser-Tyr-Ser-Arg-Tyr-Arg-Lys-Gln-Met-Ala-Val-Lys-Lys-Tyr-Leu-Ala-Ala-Val-Leu-Gly-Lys-Arg-Tyr-Lys-Gln-Arg-Val-Lys-Asn;

His-Ser-Asp-Gly-Ile-Phe-Thr-Asp-Ser-Tyr-Ser-Arg-Tyr-Arg-Lys-Gln-Met-Ala-Val-Lys-Lys-Tyr-Leu-Ala-Ala-Val-Leu-Gly-Lys-Arg-Tyr-Lys-Gln-Arg-Val-Lys-Asn-Lys; and peptides in which has the carboxy terminus has an NH$_2$ group.

2. The peptide of claim 1 having the formula His-Ser-Asp-Gly-Ile-Phe-Thr-Asp-Ser-Tyr-Ser-Arg-Tyr-Arg-Lys-Gln-Met-Ala-Val-Lys-Lys-Tyr-Leu-Ala-Ala-Val-Leu-NH$_2$.

3. The peptide of claim 1 having the formula His-Ser-Asp-Gly-Ile-Phe-Thr-Asp-Ser-Tyr-Ser-Arg-Tyr-Arg-Lys-Gln-Met-Ala-Val-Lys-Lys-Tyr-Leu-Ala-Ala-Val-Leu-Gly.

4. The peptide of claim 1 having the formula His-Ser-Asp-Gly-Ile-Phe-Thr-Asp-Ser-Tyr-Ser-Arg-Tyr-Arg-Lys-Gln-Met-Ala-Val-Lys-Lys-Tyr-Leu-Ala-Ala-Val-Leu-Gly-NH$_2$.

5. The peptide of claim 1 having the formula His-Ser-Asp-Gly-Ile-Phe-Thr-Asp-Ser-Tyr-Ser-Arg-Tyr-Arg-Lys-Gln-Met-Ala-Val-Lys-Lys-Tyr-Leu-Ala-Ala-Val-Leu-Gly-Lys.

6. The peptide of claim 1 having the formula His-Ser-Asp-Gly-Ile-Phe-Thr-Asp-Ser-Tyr-Ser-Arg-Tyr-Arg-Lys-Gln-Met-Ala-Val-Lys-Lys-Tyr-Leu-Ala-Ala-Val-Leu-Gly-Lys-NH$_2$.

7. The peptide of claim 1 having the formula His-Ser-Asp-Gly-Ile-Phe-Thr-Asp-Ser-Tyr-Ser-Arg-Tyr-Arg-Lys-Gln-Met-Ala-Val-Lys-Lys-Tyr-Leu-Ala-Ala-Val-Leu-Gly-Lys-Arg.

8. The peptide of claim 1 having the formula His-Ser-Asp-Gly-Ile-Phe-Thr-Asp-Ser-Tyr-Ser-Arg-Tyr-Arg-Lys-Gln-Met-Ala-Val-Lys-Lys-Tyr-Leu-Ala-Ala-Val-Leu-Gly-Lys-Arg-NH$_2$.

9. The peptide of claim 1 having the formula His-Ser-Asp-Gly-Ile-Phe-Thr-Asp-Ser-Tyr-Ser-Arg-Tyr-Arg-Lys-Gln-Met-Ala-Val-Lys-Lys-Tyr-Leu-Ala-Ala-Val-Leu-Gly-Lys-Arg-Tyr.

10. The peptide of claim 1 having the formula His-Ser-Asp-Gly-Ile-Phe-Thr-Asp-Ser-Tyr-Ser-Arg-Tyr-Arg-Lys-Gln-Met-Ala-Val-Lys-Lys-Tyr-Leu-Ala-Ala-Val-Leu-Gly-Lys-Arg-Tyr-NH$_2$.

11. The peptide of claim 1 having the formula His-Ser-Asp-Gly-Ile-Phe-Thr-Asp-Ser-Tyr-Ser-Arg-Tyr-Arg-Lys-Gln-Met-Ala-Val-Lys-Lys-Tyr-Leu-Ala-Ala-Val-Leu-Gly-Lys-Arg-Tyr-Lys.

12. The peptide of claim 1 having the formula His-Ser-Asp-Gly-Ile-Phe-Thr-Asp-Ser-Tyr-Ser-Arg-Tyr-Arg-Lys-Gln-Met-Ala-Val-Lys-Lys-Tyr-Leu-Ala-Ala-Val-Leu-Gly-Lys-Arg-Tyr-Lys-NH$_2$.

13. The peptide of claim 1 having the formula His-Ser-Asp-Gly-Ile-Phe-Thr-Asp-Ser-Tyr-Ser-Arg-Tyr-Arg-Lys-Gln-Met-Ala-Val-Lys-Lys-Tyr-Leu-Ala-Ala-Val-Leu-Gly-Lys-Arg-Tyr-Lys-Gln.

14. The peptide of claim 1 having the formula His-Ser-Asp-Gly-Ile-Phe-Thr-Asp-Ser-Tyr-Ser-Arg-Tyr-Arg-Lys-Gln-Met-Ala-Val-Lys-Lys-Tyr-Leu-Ala-Ala-Val-Leu-Gly-Lys-Arg-Tyr-Lys-Gln-NH$_2$.

15. The peptide of claim 1 having the formula His-Ser-Asp-Gly-Ile-Phe-Thr-Asp-Ser-Tyr-Ser-Arg-Tyr-Arg-Lys-Gln-Met-Ala-Val-Lys-Lys-Tyr-Leu-Ala-Ala-Val-Leu-Gly-Lys-Arg-Tyr-Lys-Gln-Arg.

16. The peptide of claim 1 having the formula His-Ser-Asp-Gly-Ile-Phe-Thr-Asp-Ser-Tyr-Ser-Arg-Tyr-Arg-Lys-Gln-Met-Ala-Val-Lys-Lys-Tyr-Leu-Ala-Ala-Val-Leu-Gly-Lys-Arg-Tyr-Lys-Gln-Arg-NH$_2$.

17. The peptide of claim 1 having the formula His-Ser-Asp-Gly-Ile-Phe-Thr-Asp-Ser-Tyr-Ser-Arg-Tyr-Arg-Lys-Gln-Met-Ala-Val-Lys-Lys-Tyr-Leu-Ala-Ala-Val-Leu-Gly-Lys-Arg-Tyr-Lys-Gln-Arg-Val.

18. The peptide of claim 1 having the formula His-Ser-Asp-Gly-Ile-Phe-Thr-Asp-Ser-Tyr-Ser-Arg-Tyr-Arg-Lys-Gln-Met-Ala-Val-Lys-Lys-Tyr-Leu-Ala-Ala-Val-Leu-Gly-Lys-Arg-Tyr-Lys-Gln-Arg-Val-NH$_2$.

19. The peptide of claim 1 having the formula His-Ser-Asp-Gly-Ile-Phe-Thr-Asp-Ser-Tyr-Ser-Arg-Tyr- Arg-Lys-Gln-Met-Ala-Val-Lys-Lys-Tyr-Leu-Ala-Ala-Val-Leu-Gly-Lys-Arg-Tyr-Lys-Gln-Arg-Val-Lys.

20. The peptide of claim 1 having the formula His-Ser-Asp-Gly-Ile-Phe-Thr-Asp-Ser-Tyr-Ser-Arg-Tyr-Arg-Lys-Gln-Met-Ala-Val-Lys-Lys-Tyr-Leu-Ala-Ala-Val-Leu-Gly-Lys-Arg-Tyr-Lys-Gln-Arg-Val-Lys-NH$_2$.

21. The peptide of claim 1 having the formula His-Ser-Asp-Gly-Ile-Phe-Thr-Asp-Ser-Tyr-Ser-Arg-Tyr-Arg-Lys-Gln-Met-Ala-Val-Lys-Lys-Tyr-Leu-Ala-Ala-Val-Leu-Gly-Lys-Arg-Tyr-Lys-Gln-Arg-Val-Lys-Asn.

22. The peptide of claim 1 having the formula His-Ser-Asp-Gly-Ile-Phe-Thr-Asp-Ser-Tyr-Ser-Arg-Tyr-Arg-Lys-Gln-Met-Ala-Val-Lys-Lys-Tyr-Leu-Ala-Ala-Val-Leu-Gly-Lys-Arg-Tyr-Lys-Gln-Arg-Val-Lys-Asn-NH$_2$.

23. The peptide of claim 1 having the formula His-Ser-Asp-Gly-Ile-Phe-Thr-Asp-Ser-Tyr-Ser-Arg-Tyr-Arg-Lys-Gln-Met-Ala-Val-Lys-Lys-Tyr-Leu-Ala-Ala-Val-Leu-Gly-Lys-Arg-Tyr-Lys-Gln-Arg-Val-Lys-Asn-Lys.

24. The peptide of claim 1 having the formula His-Ser-Asp-Gly-Ile-Phe-Thr-Asp-Ser-Tyr-Ser-Arg-Tyr-Arg-Lys-Gln-Met-Ala-Val-Lys-Lys-Tyr-Leu-Ala-Ala-Val-Leu-Gly-Lys-Arg-Tyr-Lys-Gln-Arg-Val-Lys-Asn-Lys-NH$_2$.

25. A pharmaceutical composition comprising at least one peptide of any one of claims 1-24 and a pharmaceutically acceptable carrier.

26. A method of stimulating adenylate cyclase activity in vertebrate cells which comprises contacting the cells with an effective amount of a peptide of anyone of claim 1-24.

* * * * *